US007326783B2

(12) United States Patent
Schlingensiepen et al.

(10) Patent No.: US 7,326,783 B2
(45) Date of Patent: Feb. 5, 2008

(54) PHARMACEUTICAL COMPOSITION COMPRISING ANTISENSE-NUCLEIC ACID FOR PREVENTION AND/OR TREATMENT OF NEURONAL INJURY, DEGENERATION AND CELL DEATH AND FOR THE TREATMENT OF NEOPLASMS

(75) Inventors: Georg-F Schlingensiepen, Gottingen (DE); Reimar Schlingensiepen, Gottingen (DE); Karl-Hermann Schlingensiepen, Gottingen (DE); Wolfgang Brysch, Gottingen (DE)

(73) Assignee: Biognostik Gesellschaft fur biomolekulare Diagnostik mbH, Gottingen (DE)

( * ) Notice: Subject to any disclaimer, the term of this patent is extended or adjusted under 35 U.S.C. 154(b) by 488 days.

(21) Appl. No.: 08/591,486

(22) PCT Filed: Jul. 6, 1994

(86) PCT No.: PCT/EP94/02218

§ 371 (c)(1),
(2), (4) Date: Jan. 11, 1996

(87) PCT Pub. No.: WO95/02051

PCT Pub. Date: Jan. 19, 1995

(65) Prior Publication Data

US 2002/0037866 A1 Mar. 28, 2002

(30) Foreign Application Priority Data

Jul. 10, 1993 (EP) .................................. 93111059

(51) Int. Cl.
C07H 21/04 (2006.01)
C07H 21/00 (2006.01)
(52) U.S. Cl. .................. 536/24.5; 536/25.3; 435/6
(58) Field of Classification Search ........... 536/24.5, 536/23.1, 24.35; 514/44; 435/6, 91.1, 375, 435/440, 325, 366, 352
See application file for complete search history.

(56) References Cited

U.S. PATENT DOCUMENTS 5,098,890 A * 3/1992 Gewirtz et al. .............. 514/44
5,225,326 A * 7/1993 Bresser et al. ............... 435/6
5,585,479 A * 12/1996 Hoke et al. ............... 536/24.5

FOREIGN PATENT DOCUMENTS

| EP | 0 305 929 | 3/1989 |
| WO | WO92/15680 | 9/1992 |
| WO | WO 94/08625 | 4/1994 |

OTHER PUBLICATIONS van Straaten F, et al. "Complete nucleotide sequence of a human c-onc gene: Deduced amino acid sequence of the human c-fos protein." PNAS 80: 3183-3187, 1983.*
Nomura N, et al. "Isolation of human cDNA clones of jun-related genes, jun-B and jun-D" Nucl. Acids Res. 18: 3047-3048, 1990.*
Hattori K, et al. "Structure and chromosomal localization of the functional intronless human JUN protooncogene." PNAS 85: 9148-9152, 1988.*
Uhlmann E, et al. "Antisense oligonucleotides: A new therapeutic principle." Chem. Rev. 90: 543-584, 1990.*
Orkin SH, et al. "Report and recommendations of the panel to assess the NIH investment in research on gene therapy.", Dec. 7, 1995.*
Stull RA, et al. "Antigene, ribozyme and aptamer nucleic acid drugs: Progress and prospects." Pharmaceutical Res. 12: 465-483, 1995.*
Gura T. "Antisense has growing pains." Science 270: 575-577, Oct. 27, 1995.*
Rojanasakul Y. "Antisense oligonucleotide therapeutics: Drug delivery and targeting." Adv. Drug Deliv. 18: 115-131, 1996.*
Colotta F, et al. "Expression and involvement of c-fos and c-jun protooncogenes in programmed cell death induced by growth factor deprivation in lumphoid cell lines." J. Biol. Chem. 267: 18278-18283, 1992.*
Oberbauer , Wien Klin Wochenschr 109/2: 40-46, 1997.*
Agrawal et al, Pharmacol. Ther. vol. 76 Nos. 1-3 pp. 151-160, 1997.*
Branch , TIBS 23 pp. 45-50, Feb. 1998.*
Block et al. "The Use of Antisense Oligonucleotides to Dissect the Role of c-fos Expression in HL-60 Cell Differentiation", pp. 71-82, from Prospects for antisense nucleic acid therapy of cancer and Aids, Ed. Wickstrom, E., 1991, Wiley-Liss, Inc., NY NY.*
McDonnell et al., Molecular and Cellular Biology, Aug. 1990, 10 (8), pp. 4248-4293.*
Pai et al., Journal of Cell Biology, 115 (3 Part 2), 1991, 207A.*
Chiasson et al. European Journal of Pharmacology—Molecular Pharmacology Section, 227 (1992) 451-453.*
Naftilan et al., Ciculation vol. 84, No. 4 (Suppl II), Oct. 1991, pp. II-338.*
Graham et al., Biotechniques vol. 13, No. 5, Nov. 1992, pp. 780-789.*
Wickstrom, E., 'Prospects for antisense nucleic acid therapy of cancer and Aids'; 1991, Wiley-Liss, Inc., New York, USA.
Pp. 83-114, Mercola, D. cited in the application, 'Antisense fos and jun RNA' see the whole document.
Erickson, R. & Izant, J. 'Gene regulation: biology of antisense RNA and DNA'; 1992 Raven Press, Ltd., New York, USA, p. 285-293.
Nature, vol. 332, Oct. 3, 1988, London GB, pp. 166-177, Angel P. et al., Oncogene jun encodes a sequence-specific transactivator . . . .

(Continued)

Primary Examiner—Richard Schnizer
Assistant Examiner—Tracy Vivlemore
(74) Attorney, Agent, or Firm—Jacobson Holman PLLC

(57) ABSTRACT

A pharmaceutical composition comprising an effective amount of a compound which is capable from preventing and treating neuronal injury, degeneration, cell death and/or neoplasms in which expression of c-jun, c-fos or jun-B plays a causal role which compound being an antisense nucleic acid or effective derivative thereof, said antisense nucleic acid hybridizing with an area of the messenger RNA (mRNA) and/or DNA encoding c-jun, c-fos or jun-B.

2 Claims, 13 Drawing Sheets

OTHER PUBLICATIONS

Figure 1:
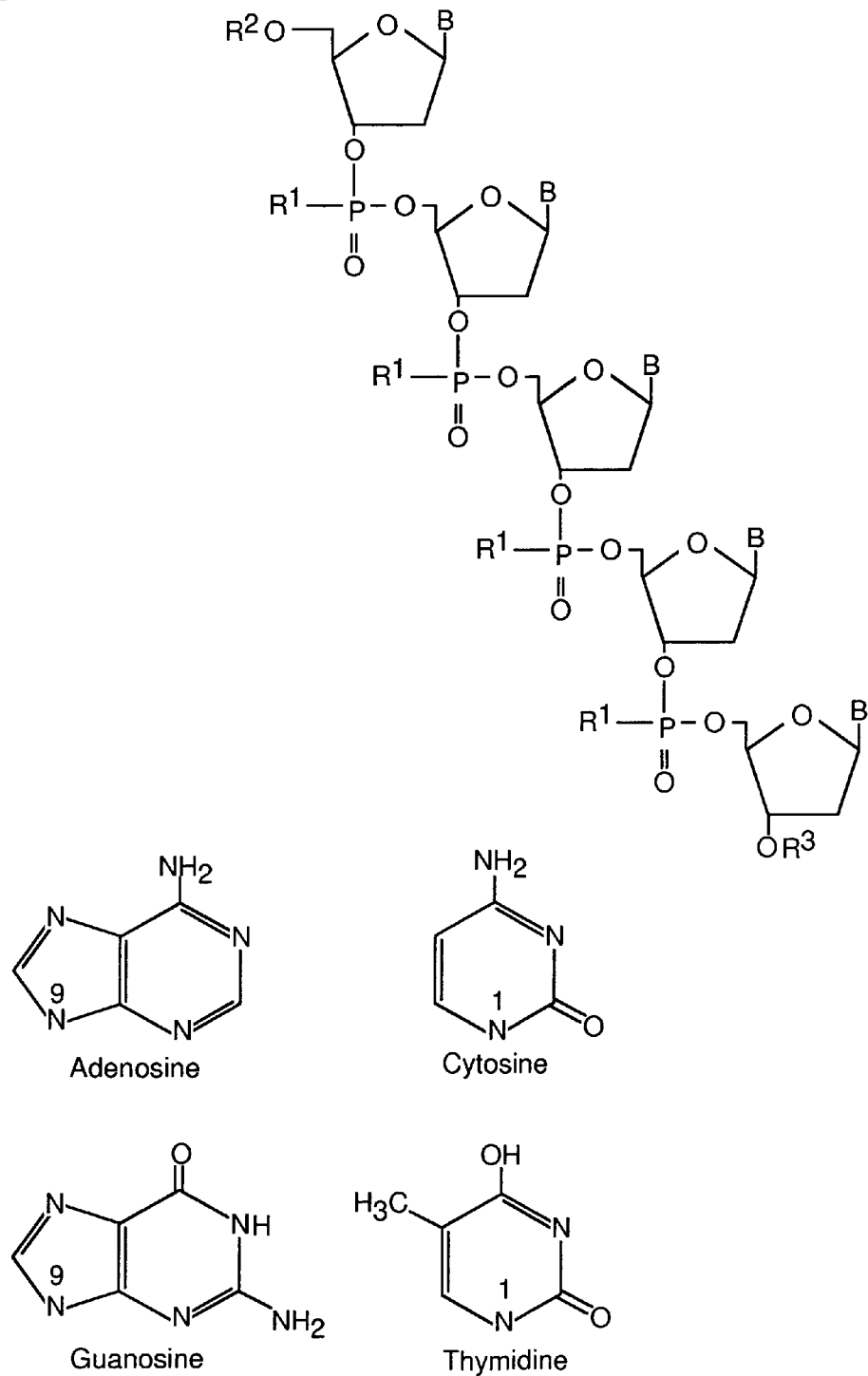

Journal of Biological Chemistry, vol. 267, No. 27, Sep. 25, 1992, Balt. MD, US, pp. 19665-19672, Nicolaides N. et al., The Jun family . . . .

Proceedings of the Am. Assoc. for Cancer Research, vol. 32, Mar. 1991 p. 303, Schlingensiepen, K.-H. & Brysch, W., Proto-oncogenes . . . .

Journal of Cellular Biochmistry, vol. 17A, 1993, p. 208 Schlingensiepen, K.-H. et al., Function of junB and c-jun in the . . . .

Biomedicine & Pharmacotherapy, vol. 46, No. 5-7, 1992, p. 257 Schlingensiepen, K.-H. & Brysch, W. Specific inhibition of . . . .

Developmental Genetics, vol. 14, Sep. 20, 1993, pp. 305-312 Schlingensiepen, K.-H. et al. Opposite function of jun-B and . . . .

Ratajczak, et al., "In vivo treatment of human leukemia in a scid mouse model with c-myb antisense oligodeoxynucleotides," Proc Natl Acad Sci USA, 89(24):11823-7, Dec. 15, 1992, Abstract only.

Schlingensiepen, et al., "Intl Conference on Antisense Nucleic Acids—Current Techniques for the Specific Inhibition of Gene Expression in Biological Analysis and Therapeutic Applications," Feb. 28-Mar. 4, 1993, Garmisch-Partenkirchen, Germany.

Schlingensiepen, et al., "Antisense—From Technology to Therapy," Blackwell Science Ltd., vol. 6, p. 290-292, 1997.

Schlingensiepen, K.H. et al., J Cell Biochem, vol. 17A, 1993 p. 208 (abstruct B977).

Schlingensiepen, K.H. et al., Biomedicine & Pharmacotherapy, vol. 46, No. 5-7, 1992 p. 257.

Schlingensiepen, K.H., et al., Proceedings of the American Association for Cancer Research, vol. 32, Mar. 1991, p. 303.

Wickstrom, E., "Prospects for antisense nucleic acid therapy of cancer and AIDS," Wiley-Liss, Inc., New York, USA, 1991, pp. 83-114, Mercola, D.

Erickson, R. & Izant, J., "Gene regulation: biology of antisense RNA and DNA," Raven Press, Ltd., New York, USA, 1992, pp. 285-293, Bradley, M. et al.

* cited by examiner

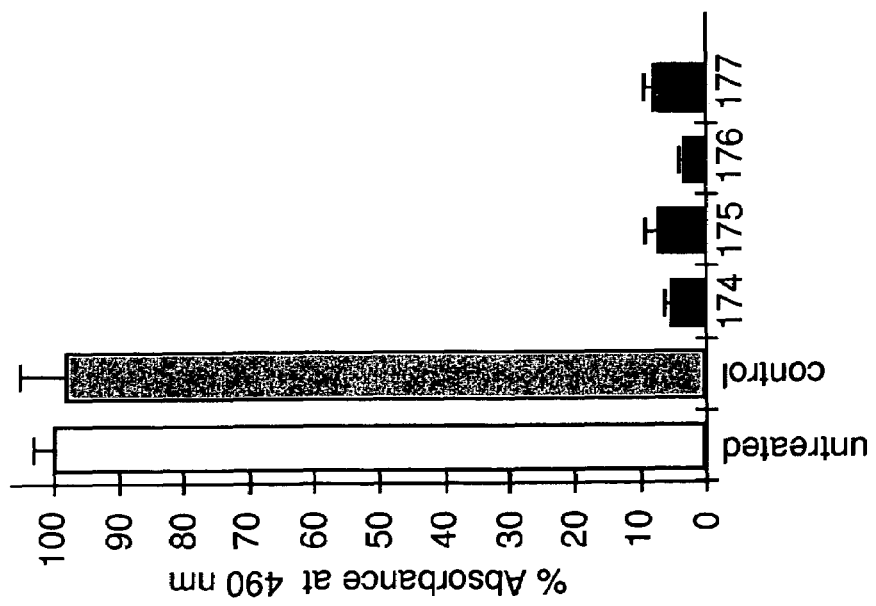
Fig. 5A  Inhibition of rat c-Jun protein expression

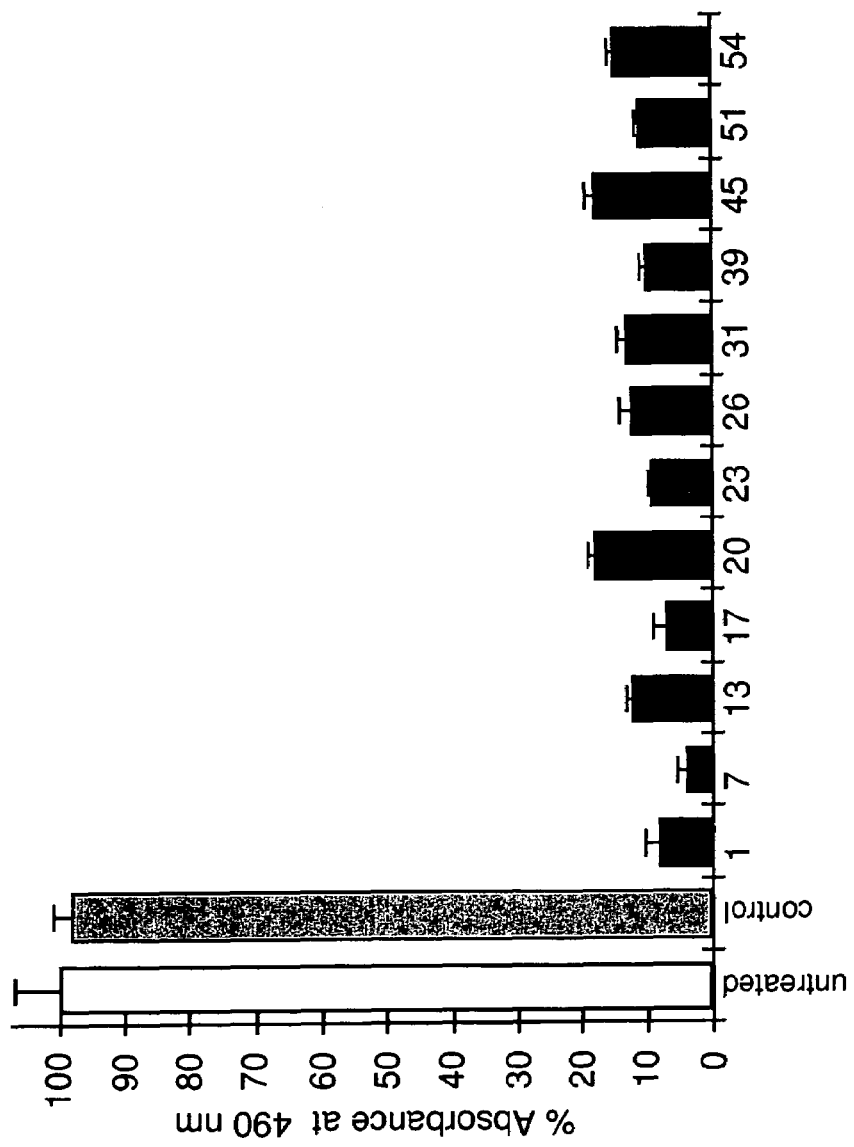
Fig. 5B Inhibition of human c-Jun protein expression

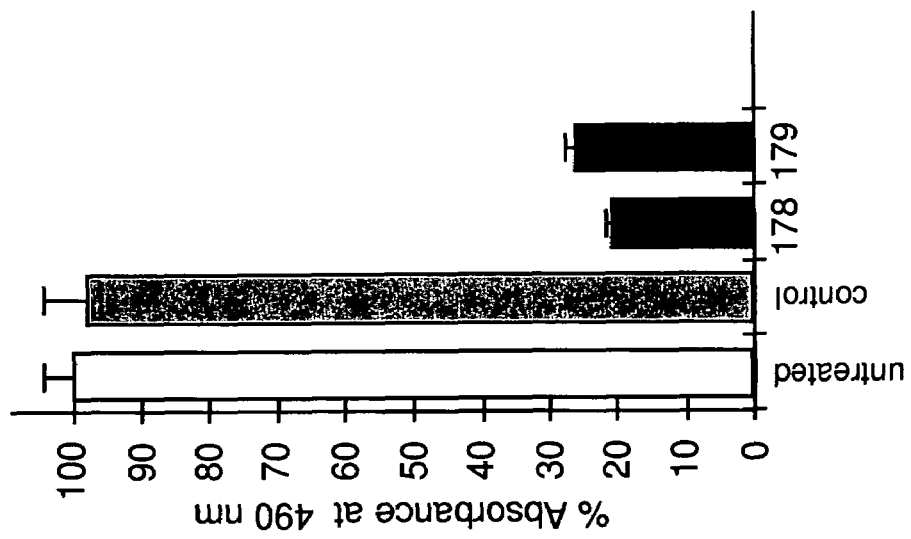
Fig. 5C Inhibition of rat Jun-B protein expression

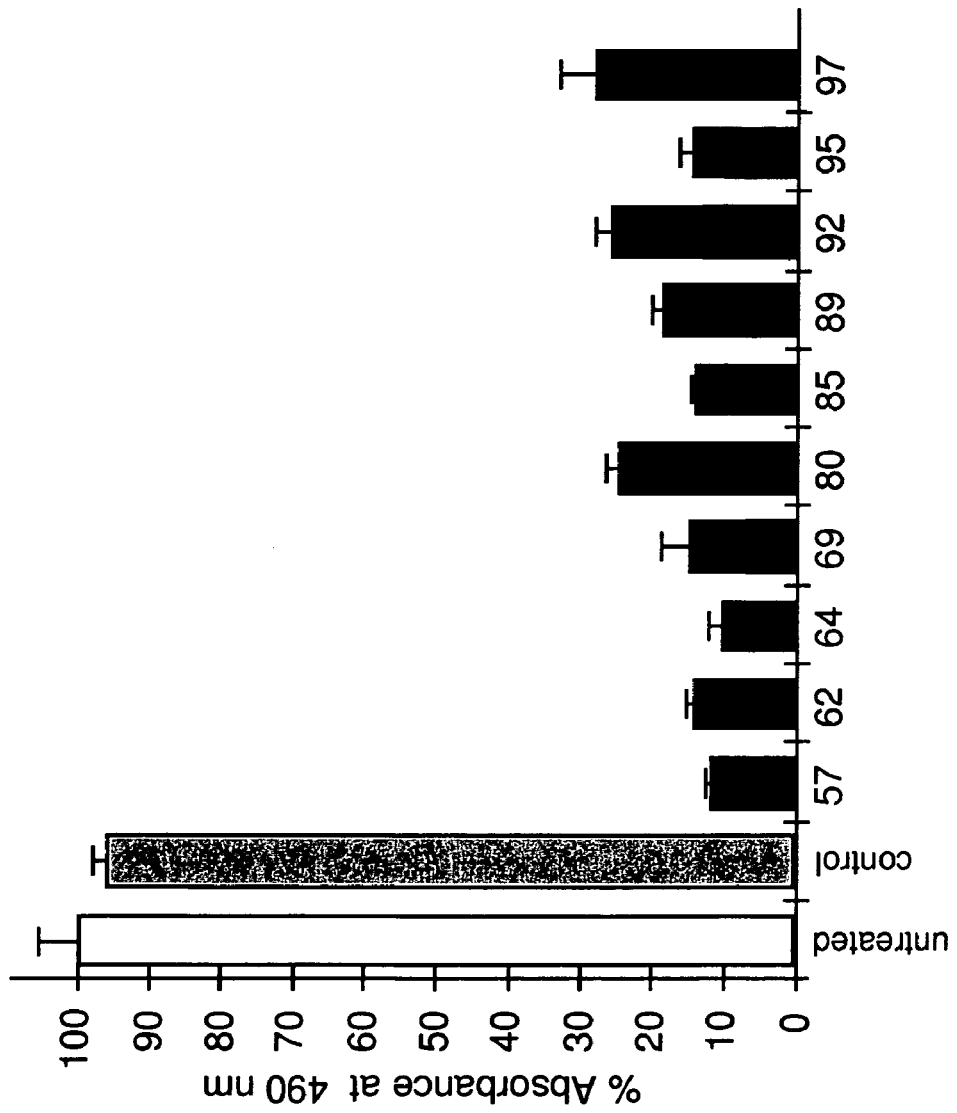

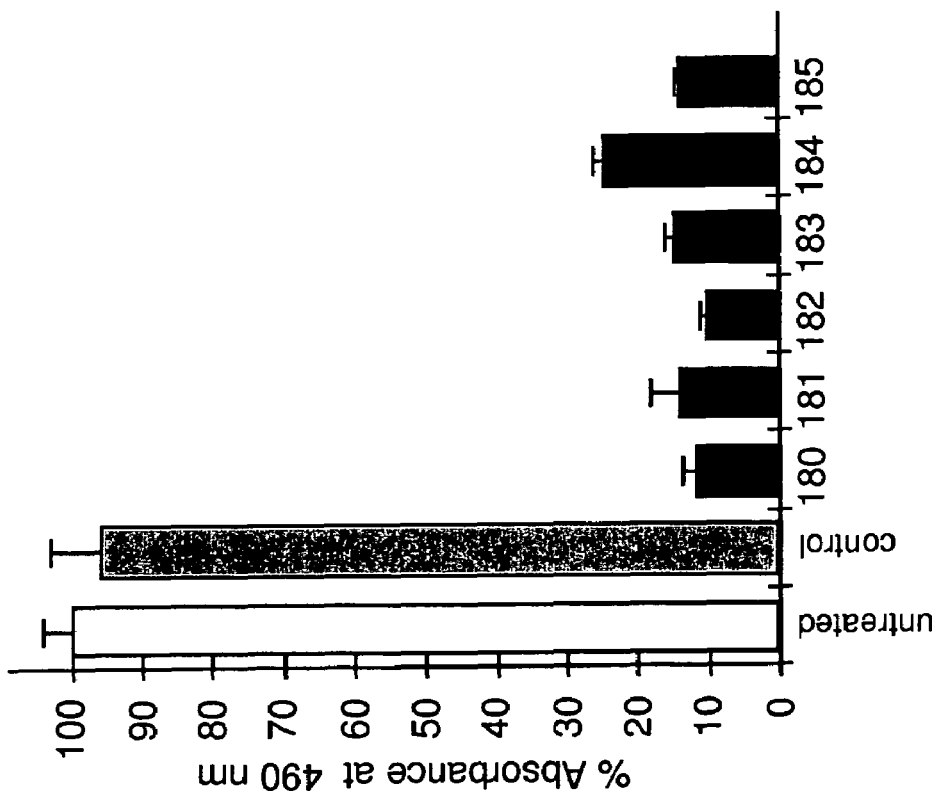
Fig. 5E Inhibition of rat c-Fos protein expression

Fig. 5F Inhibition of human c-Fos protein expression

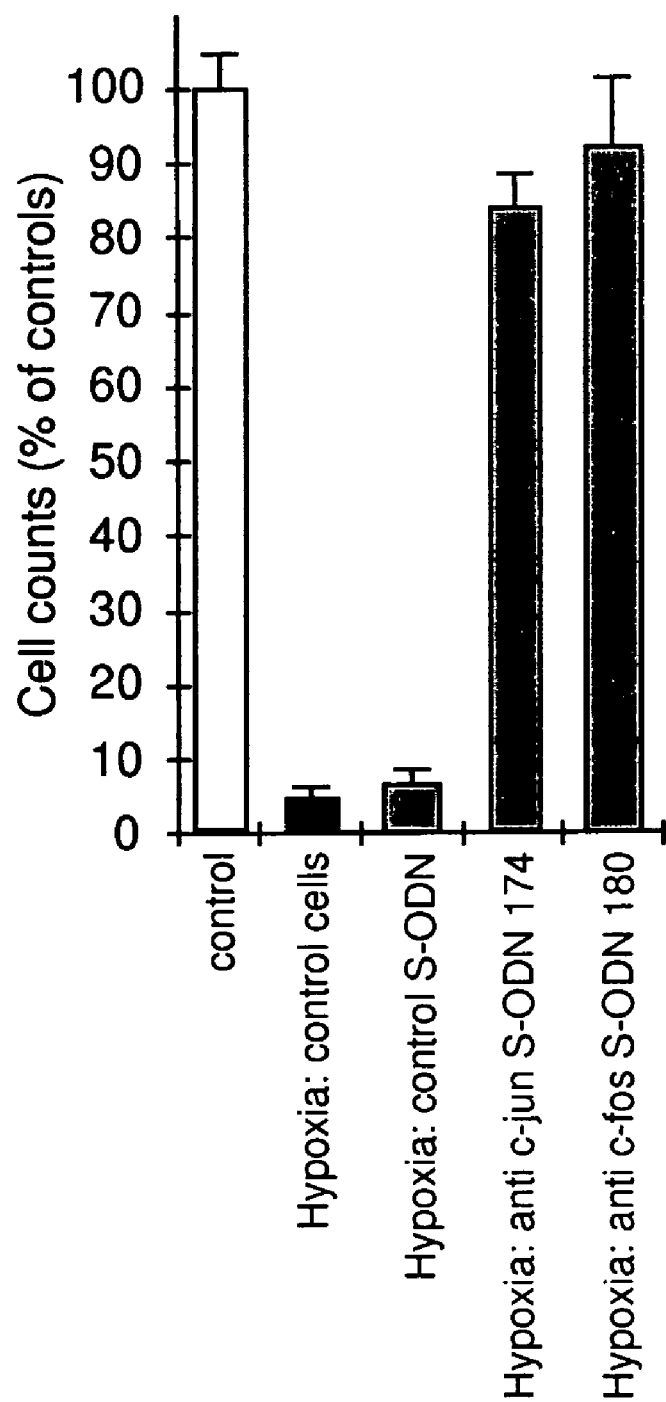
Fig. 6 Neuronal Survival

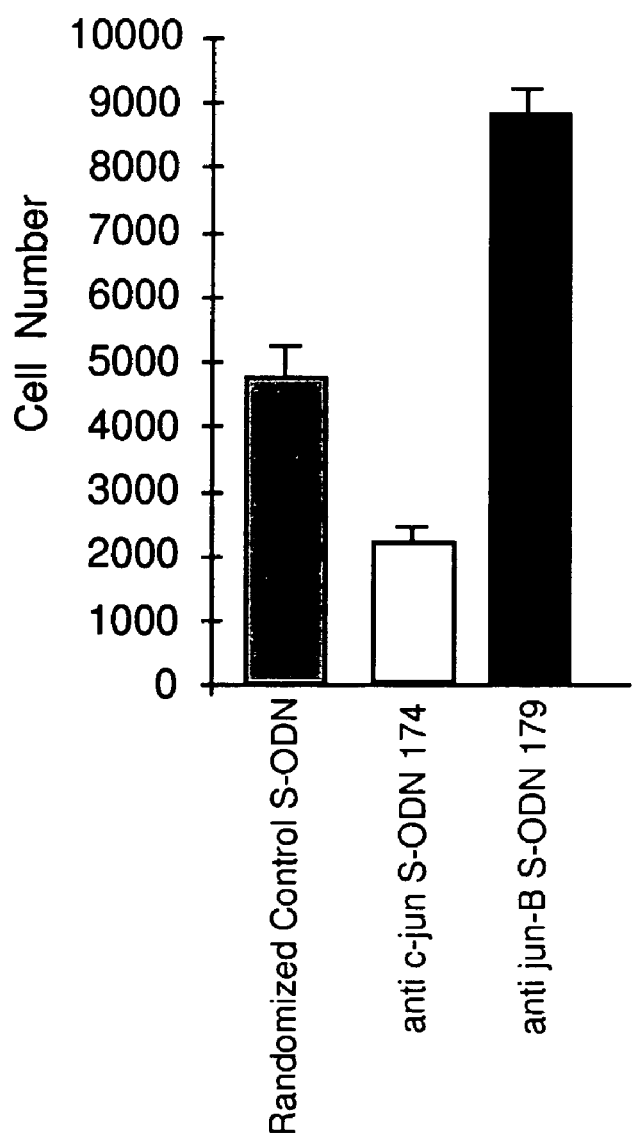
Fig. 7 Cell number of PC-12 tumor-cells after induction of differentiation Fig. 8
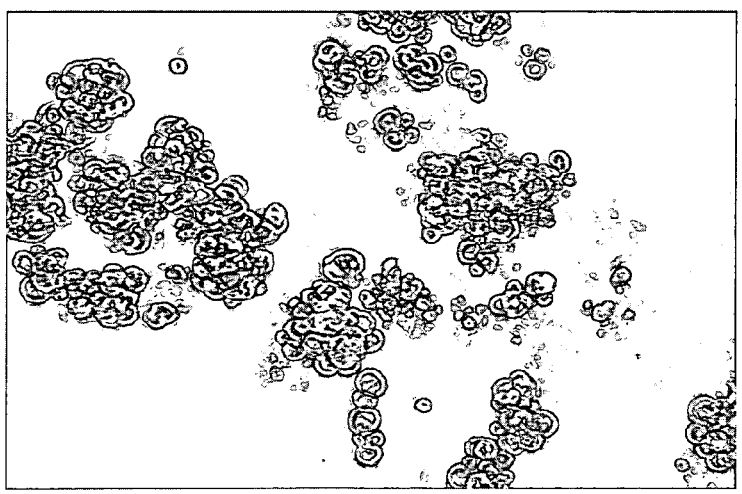
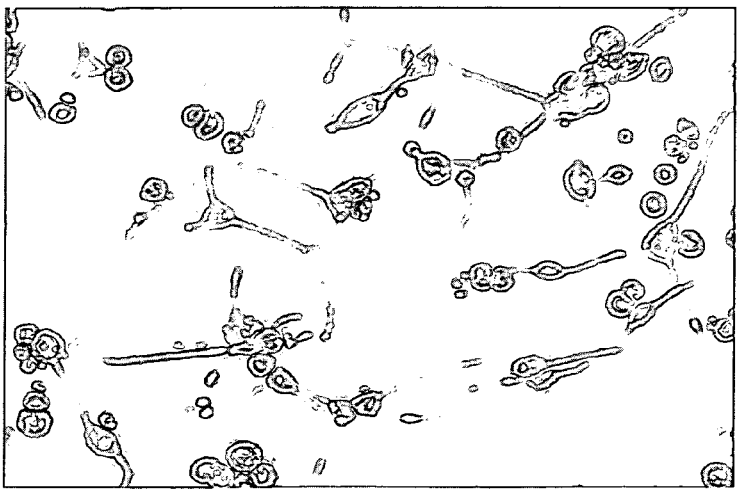

PHARMACEUTICAL COMPOSITION COMPRISING ANTISENSE-NUCLEIC ACID FOR PREVENTION AND/OR TREATMENT OF NEURONAL INJURY, DEGENERATION AND CELL DEATH AND FOR THE TREATMENT OF NEOPLASMS

This is a 371 of PCT/EP94/02218, filed Jul. 10, 1993.

The present invention is related to a pharmaceutical composition and a diagnostic agent comprising an effective amount of a compound which is capable of preventing and treating neuronal injury, cell death and/or neoplasms in which expression of c-jun, c-fos or jun-B plays a causal role, particularly, antisense nucleic acid or -oligonucleotides hybridizing with an area of the messenger RNA (mRNA) and/or DNA comprising the genes for c-jun, c-fos or jun-B; the use of the compound for the preparation of a pharmaceutical composition for the treatment of neoplasms and/or the prevention and/or treatment of neuronal injury and degeneration related with the expression of c-jun, c-fos or jun-B.

Schlingensiepen et al. report in Proceedings of the American Association for Cancer Research, Vol. 32, p. 303, Abstract No. 1799, 82. Annual Meeting of the American Association for Cancer Research, Houston, USA, 1991 that c-jun and jun-B genes share high sequence homology with the v-jun gene. They belong to the immediate early gene group. C-jun together with c-fos constitutes the DNA binding factor AP-1. C-jun and jun-B expression was inhibited in different cell lines using phosphorothioate oligodeoxynucleotides. C-jun inhibition strongly reduced 3H-thymidine incorporation in two mammary carcinoma cell lines, in the rat phaeochromocytoma cell line PC-12 and in NH 3T3 mouse fibroblasts. The inhibition of c-jun expression and of c-fos expression had very similar effects in the same cell lines inhibition of jun-B expression drastically increases 3H-thymidine uptake to more than 10 fold. 10-jun is meant to have the characteristics of a proto-oncogene but jun-B appears to be an anti-oncogene with strong anti-proliferative action similar to that of p53. The results suggest that jun-B and c-jun to be functional antagonists with regard to their effect on cell growth. This investigation was carried out in order to elucidate the function of respective genes and proteins. This abstract does not suggest any therapeutic concept.

From the Journal of Cellular Biochemistry, Abstract B 977, Keystone Symposia on Molecular & Cellular Biology, 1993, Schlingensiepen et al. report of two homologues of the proto-oncogene c-jun which have been identified in mammals. In that abstract it is speculated that jun-B may play a role in cell-differentiation. In order to investigate functional questions of the jun-B gene antisense phosophorothioate oligo-deoxynucleotides (S-ODN) have been used to specifically inhibit expression of c-jun and jun-B in neuronally differentiating PC-12 tumor cells in primary neuronal cell cultures from the rat hippocampus. Western blot analysis revealed specific reductions in the respective Jun protein levels by more than 90% after application of 2 µM S-ODN. In neuronal cell cultures neurite outgrowth was strongly inhibited after inhibition of jun-B expression but was enhanced after application of anti c-jun-S-ODN. Even more drastic changes were observed in neuronally differentiating PC-12 tumor cells. The results suggest that jun-B plays a crucial role in cell differentiation while c-jun appears to inhibit differentiation. A therapeutic concept is also not available from that disclosure.

From Biomedicine & Pharmacotherapy, Abstract 38, from the 5. International Congress on Differentiation Therapy, Schlingensiepen et al. report also about the results published in Journal of Cellular Biochemistry.

In Developmental Genetics 14: 305-312 (1993) Schlingensiepen et al. report about the induction of the jun-B and/or c-jun transcription factors. The induction is part of the immediate early response to diverse stimuli that induce alterations in cellular programs. In order to determine functional significance of the jun-B and/or c-jun transcription antisense phosphorothioate oligodeoxynucleotides were used to inhibit the expression of the genes in proliferating and neuronally differentiating cells. In cell culture studies it was found that inhibition of jun-B expression markedly reduced morphological differentiation. Conversely, inhibition of c-jun proteins synthesis enhanced morphological differentiation of both primary neurons and PC-12 tumor cells.

EP-A-0 305 929 deals with membranes with bound oligonucleotides and peptides directly bound onto the membrane. The method for synthesizing oligonucleotides directly bound onto a membrane provides a means for generating membrane affinity supports. A modified membrane for the method of direct synthesis is also provided.

WO 92/15680 deals with a method and compositions for the selective inhibition of gene expression. Disclosed are methods and compositions for the selective inhibition gene expression through the application of antisense RNA technology. Antisense RNA constructs employ the use of antisense intron DNA corresponding to distinct intron regions of the gene whose expression is targeted for down-regulation. In an exemplary embodiment a human lung cancer cell line (NCI-H460a) with a homozygous spontaneous K-ras mutation was transfected with a recombinant plasmid that synthesizes a genomic segment of K-ras in antisense orientation. Translation of the mutated K-ras m RNA was specifically inhibited, whereas expression of H-ras and N-ras was unchanged. A three-fold growth inhibition occurred in H460a cells when expression of the mutated ras p21 protein was down-regulated by antisense RNA and cells remained viable. The growth of H460a tumors in nu/nu mice was substantially reduced by expressed K-ras antisense RNA.

Dan Mercola in Prospects for Antisense Nucleic Acid Therapy of Cancer and AIDS, pp. 83-114, 1991 deals with the use of antisense fos RNA and, to a lesser extent, antisense jun RNA. Such antisense RNA has contributed to understanding of the roles of gene products in cell cyle regulation, differentiation and so on. Progess in the application of antisense RNA and oligonucleotides to these topics and implications for diagnostic and therapeutic approaches are considered.

S. van den Berg in Prospects for Antisense Nucleic Acid Therapy and Cancer and AIDS, pp. 63-70, 1991 deals with antisense fos oligodeoxyribonucleotides suppressing the generation of chromosomal aberrations. The fast induction of the expression product FOS nuclear onco-protein by serum treatment of starved cells was used to test the functional stability of antisense oligodeoxyribonucleotides. Unmodified oligodeoxyribonucleotides lost their blocking effect with a half-life of about 2 hours, modification of the backbone by thioesters extended the half-life to about 4 hours. The modified oligodeoxyribonucleotides where used to unravel a decisive role of FOS in a complex physiologic event: The induction of chromosomal aberrations upon overexpression of oncogenes like ras and mos and upon irradiation of fibroblasts with UV-light.

Induction of the c-Fos, Jun-B and/or c-Jun transcription factors is part of the immediate early response to diverse stimuli that induce alterations in cellular programs. C-jun and c-fos are proto-oncogenes whose expression is required for induction of cell proliferation while the function of the Jun-B transcription factor has remained unclear.

Neuronal cell injury and cell death due e.g. to hypoxia or hypoglycemia may occur in cause of responses of the cell to diverse stimuli inducing alterations in cellular programs.

It is an object of the present invention to provide a pharmaceutical composition for the prevention and/or treatment of neuronal injury and/or cell death. Surprisingly, the expression of the c-fos and c-jun gene plays a causal role in neuronal cell injury and cell death due e.g. to hypoxia or hypoglycemia.

Furthermore, surprisingly, expression of the Jun-B protein is required for the differentiation of normal and neoplastic cells and inhibition of c-Jun protein expression enhances the differentiation of such cells. Based on that result the present invention provides a pharmaceutical compositon for the treatment of neoplasms by enhancing jun-B expression and/or inhibiting c-jun expression.

A pharmaceutical composition comprising antisense nucleic acids or effective derivatives thereof which hybridize with an area of the mRNAs or DNA comprising the genes for c-jun, c-fos or jun-B are able to solve the problems addressed above. The antisense nucleic acid is able to hybridize with regions of the c-jun, jun-B or c-fos mRNAs. It is understood by the skilled person that fragments of the antisense nucleic acids and antisense nucleic acids containing these sequences work according to the invention so long as production of the c-Jun and/or c-Fos and/or Jun-B proteins is reduced or inhibited.

According to the invention the antisense-oligonucleotides are obtainable by solid phase synthesis using phosphite triester chemistry by growing the nucleotide chain in 3'-5' direction in that the respective nucleotide is coupled to the first nucleotide which is covalently attached to the solid phase comprising the steps of
  cleaving 5'DMT protecting group of the previous nucleotide,
  adding the respective nucleotide for chain propagation,
  modifying the phosphite group subsequently cap unreacted 5'-hydroxyl groups and
  cleaving the oligonucleotide from the solid support,
  followed by working up the synthesis product.

Figure 2:
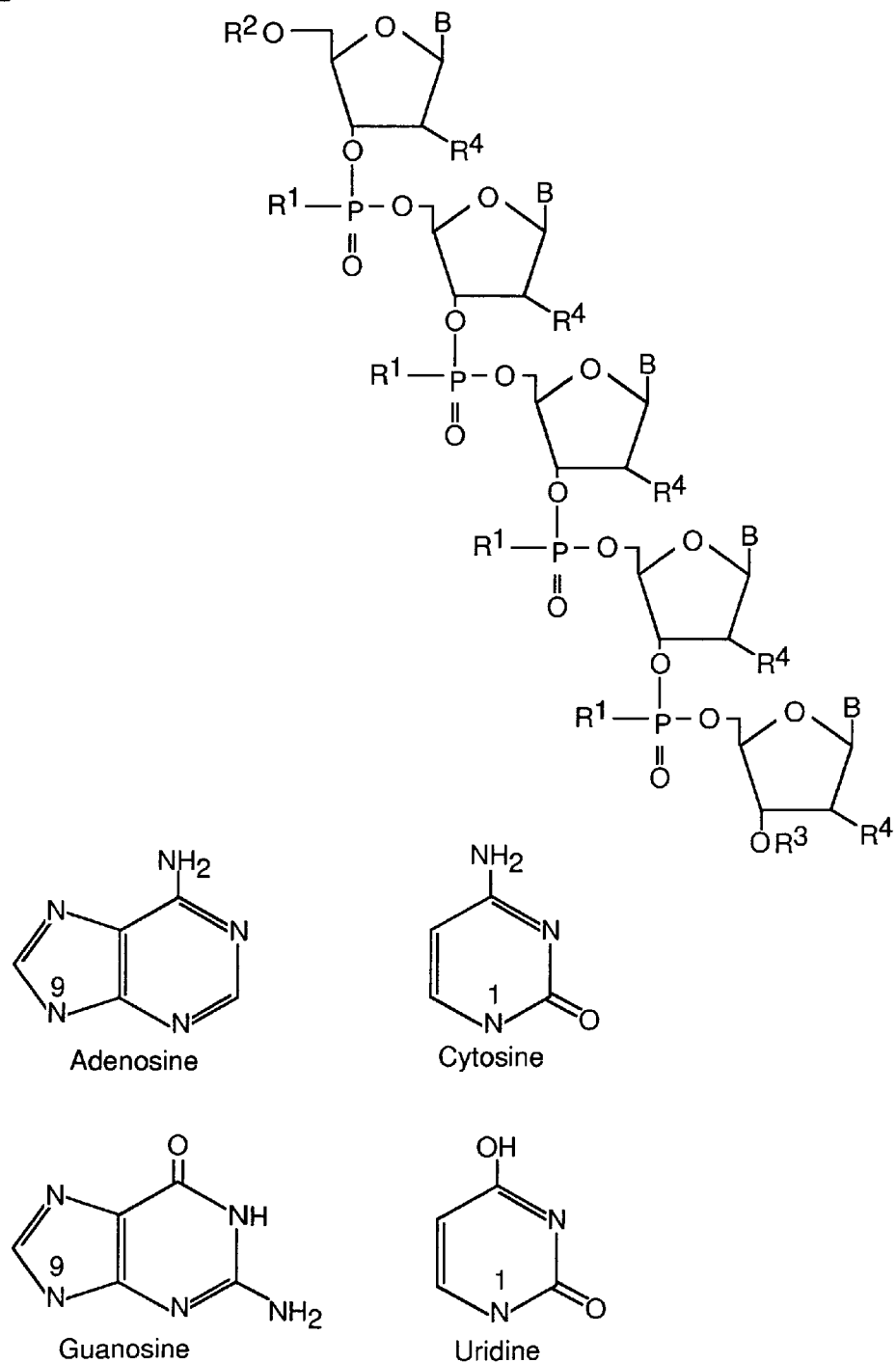
Figure 3:
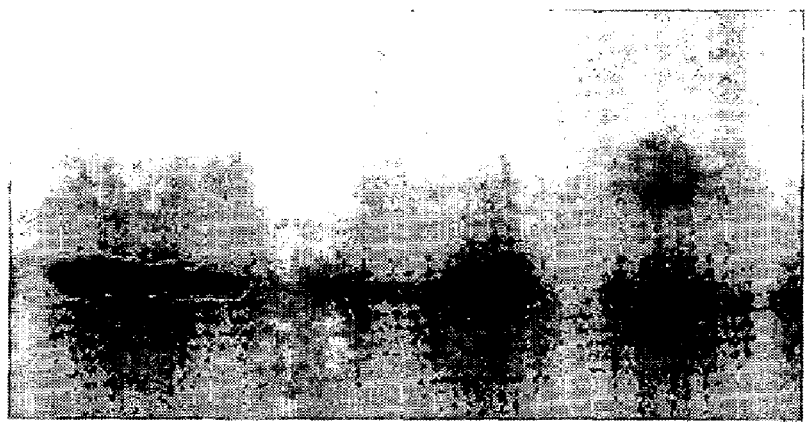
Figure 4:
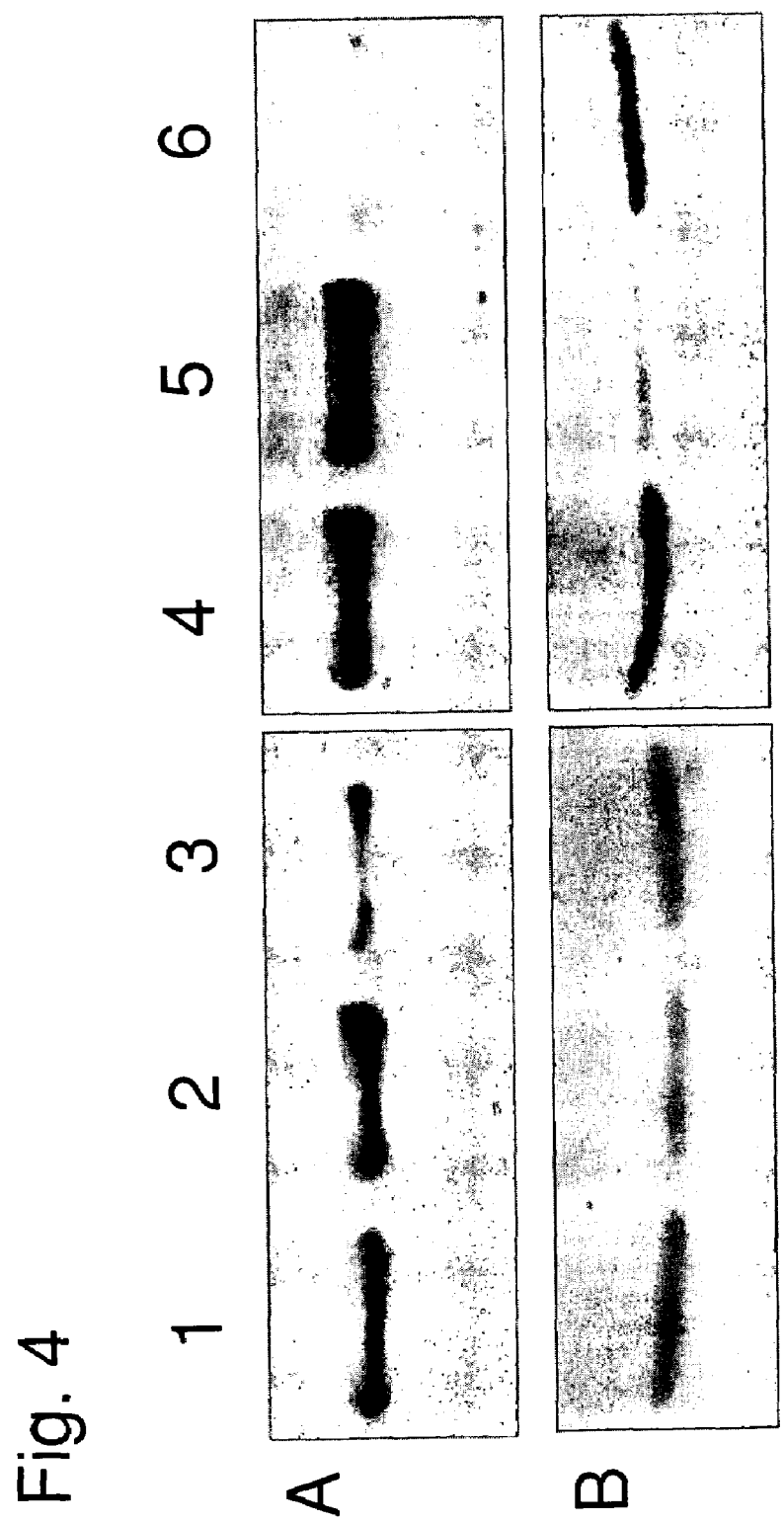

The chemical structures of oligodeoxy-ribonucleotides are given in FIG. 1 as well as the respective structures of antisense oligo-ribonucleotides are given in FIG. 2. The oligonucleotide chain is to be understood as a detail out of a longer nucleotide chain.

In FIG. 1 lit. B means an organic base such as adenine (A), guanine (G), cytosine (C) and thymine (T) which are coupled via N9 (A,G) or N1 (D,T) to the desoxyribose. The sequence of the bases is the reverse complement of the genetic target sequence (mRNA-sequence). The modifications used are 1. Oligodeoxy-ribonucleotides where all $R^1$ are substituted by
  1.1 $R^1=O$
  1.2 $R^1=S$
  1.3 $R^1=F$
  1.4 $R^1=CH_3$
  1.5 $R^1=OEt$ 2. Oligodeoxy-ribonucleotides where $R^1$ is varied at the internucleotide phosphates within one oligonucleotide

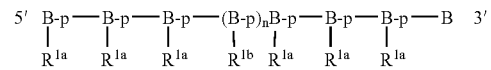

where B=deoxy-ribonucleotide dA, dC, dG or dT depending on gene sequence
  p=internucleotide phosphate
  n=an oligodeoxy-ribonucleotide stretch of length 6-20 bases
  2.1 $R^{1a}=S; R^{1b}=O$
  2.2 $R^{1a}=CH_3; R^{1b}=O$
  2.3 $R^{1a}=S; R^{1b}=CH_3$
  2.4 $R^{1a}=CH_3; R^{1b}=S$ 3. Oligodeoxy-ribonucleotides where $R^1$ is alternated at the internucleotide phosphates within one oligonucleotide

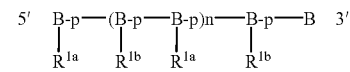

where B=deoxy-ribonucleotide dA, dC, dG or dT depending on gene sequence
  p=internucleotide phosphate
  n=an oligodeoxy-ribodinucleotide stretch of length 4-12 dinucleotides
  3.2 $R^{1a}=S; R^{1b}=O$
  3.2 $R^{1a}=CH_3; R^{1b}=O$
  3.3 $R^{1a}=S; R^{1b}=CH_3$ 4. Any of the compounds 1.1-1.5; 2.1-2.4; 3.1-3.3 coupled at $R^2$ with the following compounds which are covalently coupled to increase cellular uptake
  4.1 cholesterol
  4.2 poly(L)lysine
  4.3 transferrin
  4.4 folic acid 5. Any of the compounds 1.1-1.5; 2.1-2.4; 3.1-3.3 coupled at $R^3$ with the following compounds which are covalently coupled to increase cellular uptake
  5.1 cholesterol
  5.2 poly(L)lysine
  5.3 transferrin
  5.4 folic acid In the case of the RNA-oligonucleotides (FIG. 2) are the basis (adenine (A), guanine (G), cytosine (C), uracil (U)) coupled via N9 (A,G) or N1 (C,U) to the ribose. The sequence of the basis is the reverse complement of the genetic target sequence (mRNA-sequence). The modifications in the oligo-nucleotide sequence used are as follows 6. Oligo-ribonucleotides where all $R^1$ are substituted by
  6.1 $R^1=O$
  6.2 $R^1=S$
  6.3 $R^1=F$
  6.4 $R^1=CH_3$
  6.5 $R^1=OEt$ 7. Oligo-ribonucleotides where $R^1$ is varied at the internucleotide phosphates within one oligonucleotide

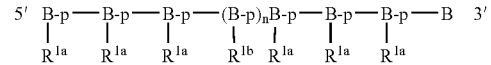

where B=ribonucleotide A, C, G or T depending on gene sequence
p=internucleotide phosphate
n=an oligo-ribonucleotide stretch of length 4-20 bases
7.1 $R^{1a}=S$; $R^{1b}=O$
7.2 $R^{1a}=CH_3$; $R^{1b}=O$
7.3 $R^{1a}=S$; $R^{1b}=CH_3$
7.4 $R^{1a}=CH_3$; $R^{1b}=S$
8. Oligo-ribonucleotides where $R^1$ is alternated at the internucleotide phosphates within one oligonucleotide

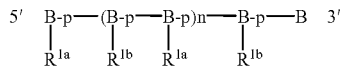

where B=ribonucleotide A, C, G or T depending on gene sequence
p=internucleotide phosphate
n=an oligo-ribodinucleotide stretch of length 4-12 dinucleotides
8.2 $R^{1a}=S$; $R^{1b}=O$
8.2 $R^{1a}=CH_3$; $R^{1b}=O$
8.3 $R^{1a}=S$; $R^{1b}=CH_3$
9. Any of the compounds 6.1-6.5; 7.1-7.4; 8.1-8.3 coupled at $R^2$ with the following compounds which are covalently coupled to increase cellular uptake
9.1 cholesterol
9.2 poly(L)lysine
9.3 transferrin
10. Any of the compounds 6.1-6.5; 7.1-7.4; 8.1-8.3 coupled at $R^3$ the following compounds are covalently coupled to increased cellular uptake
10.1 cholesterol
10.2 poly(L)lysine
10.3 transferrin
11. Any of the compounds 6.1-6.5; 7.1-7.4; 8.1-8.3; 9.1-9.3; 10.1-10.3 where all $R^4$ are substituted by
11.1 $R^4=O$
11.2 $R^4=F$
11.3 $R^4=CH_3$ In a preferred embodiment the c-jun antisense nucleic acid comprising the sequences as identified in the sequence listing, Seq. ID. No. 1-55 and 174-177.

In a preferred embodiment the jun-B antisense nucleic acids is comprising the sequences as identified in the sequence listing Seq. ID No. 56-97 and 178, 179.

In another preferred embodiment the c-fos antisense nucleic acid is comprising the sequences as identified in the sequence listing under Seq. ID No. 98-173 and 180-185.

It is possible that one single individual sequence as mentioned above works as an antisense nucleic acid or oligo-nucleotide structure according to the invention. However, it is also possible that one strand of nucleotides comprises more than one of the sequences as mentioned above directly covalently linked or with other nucleotides covalently linked inbetween. Preferably, individual oligo-nucleotides of the sequences as outlined in the sequence listing are addressed.

The sequence

5'GTCCCTATAC GAAC 3'(SEQ IN NO: 186)

served as randomized control sequence.

In a preferred embodiment of these oligo-nucleotides they are phosphorotioate derivatives.

Modifications of the antisense-oligonucleotides are advantageous since they are not as fast destroyed by endogeneous factors when applied as this is valid for naturally occuring nucleotide sequences. However, it is understood by the skilled person that also naturally occuring nucleotides having the disclosed sequence can be used according to the invention. In a very preferred embodiment the modification is a phosphorothioate modification.

The synthesis of the oligodeoxy-nucleotide of the invention is described as an example in a greater detail as follows.

Oligodeoxy-nucleotides were synthesized by stepwise 5'-addition of protected nucleosides using phosphite triester chemistry. The nucleotide A was introduced as 5'dimethoxy-trityl-deoxyadenosine(N-benzoyl)-N,N'-diisopropyl-2-cy-ano-ethyl phosphoramidite (0.1 M); C was introduced by a 5'-dimethoxytrityl-deoxycytidine($N^4$-benzoyl)-N,N'-diiso-propyl-2-cyanoethyl phosphoramidite; G was introduced as 5'-dimethoxy-trityl-deoxyguanosine($N^8$-isobutyryl)-N,N'-diisopropyl-2-cyanoethyl phosphoramidite and the T was introduced as 5'-dimethodytrityl-deoxythymidine-N,N'-di-isopropyl-2-cyanoethyl phosphoramidite. The nucleosides were preferably applied in 0.1 M concentration dissolved in acetonitrile.

Synthesis was performed on controlled pore glass particles of approximately 150 μm diameter (pore diameter 500 Å) to which the most 3' nucleoside is covalently attached via a long-chain alkylanin linker (average loading 30 μmol/g solid support).

The solid support was loaded into a cylindrical synthesis column, capped on both ends with filters which permit adequate flow of reagents but hold back the solid synthesis support. Reagents were delivered and withdrawn from the synthesis column using positive pressure of inert gas. The nucleotides were added to the growing oligonucleotide chain in 3'→5' direction. Each nucleotide was coupled using one round of the following synthesis cycle:

Cleave 5'DMT (dimethoxytrityl) protecting group of the previous nucleotide with 3-chloroacetic acid in dichloromethane followed by washing the column with anhydrous acetonitrile. Then simultaneously one of the bases in form of their protected derivative depending on the sequence was added plus tetrazole in acetonitrile. After reaction the reaction mixture has been withdrawn and the phosphite was oxidized with a mixture of sulfur ($S_8$) in carbon disulfid/pyridine/-triethylamine. After the oxidation reaction the mixture was withdrawn and the column was washed with acetonitrile. The unreacted 5'-hydroxyl groups were capped with simultaneous addition of 1-methylimidazole and acetic anhydryide/lutidine-/tetrahydrofuran. Thereafter, the synthesis column was washed with acetonitrile and the next cycle was started.

The work up procedure and purification of the synthesis products occured as follows.

After the addition of the last nucleotide the deoxynucleotides were cleaved from the solid support by incubation in ammonia solution. Exocyclic base protecting groups were removed by further incubation In ammonia. Then the ammonia was evaporated under vacuum. Full-length synthesis products still bearing the 5'DMT protecting group were separated from shorter failure contaminants using reverse phase high performance liquid chromatography on silica $C_{18}$ stationary phase. Eluents from the product peak were collected, dried under vacuum and the 5'-DMT protecting group cleaved by incubation in acetic acid which was evaporated thereafter under vacuum. The synthesis products were solubilized in the deionized water and extracted three times with diethylether. Then the products were dried in vacuo. Another HPLC-AX chromatography was performed and the eluents from the product peak were dialysed against excess of Trisbuffer as well as a second dialysis against deionized water. The final products were lyophilized and stored dry.

The antisense nucleic acids of the invention are intermediate products of the pharmaceutical composition or medicament of the invention. This medicament can be used for treating and/or preventing neuronal cell death, for treating neoplasms in which the expression of c-jun and/or jun-B or c-fos is of relevance for the pathogenicity. The pharmaceutical composition may comprise besides the effective compound(s) suitable carrier agents, solvents and other ingredients known in the art for producing medicaments. Preferably, these agents facilitate the adminstration of the pharmaceutical composition of the invention. Typically, the pharmaceutical composition is administered as i.v. infusion or i.v. bolus injection. The amount of the active ingredient to be adminstered is typical in the range of 0.2-50 mg of the oligonucleotide per kg body weight per day, in particular 1-12 mg/kg body weight per day.

The effect of antisense oligo-nucleotides specific for c-jun, jun-B and c-fos on protection against neuronal cell death was investigated. It was demonstrated that that c-fos as well as c-jun play a causal role in neuronal cell death. Also the role of these gene in the differentiation and proliferation of neoplastic cells was investigated. It was demonstrated that inhibition of c-Jun protein synthesis could enhance differentiation of neoplastic cells. It was demonstrated that antisense oligodeoxynucleotides as well as phosphorothioate modified nucleic acids, complementary to the mRNAs of c-jun, jun-B and c-fos specifically inhibit expression of the respective proteins.

In principal the compound which can be used as an active compound in the phamaceutical composition can be used as a diagnostic tool for evaluating whether the respective genes are exprersses. Typically, a radio active label nucleotides are hybridized by the method of northern blotting with is well-known in the art or in situ with a sample to be examined. The degree of hybridization is a measure for the degree of expression of the respective genes.

FIG. 3

Western blot analysis of rat PC-12 cell lysates. Effects of different phosphorothioate oligodeoxynucleotides on c-Fos protein expression. Incubation time with oligodeoxynucleotide were 6 h. Lane 1: randomized control S-ODN; Lane 2: anti-c-fos S-ODN-180; Lane 3: anti-c-fos S-ODN-182. 10 μg of total protein were used per lane.

FIG. 4

Effects of different phosphorothioate oligodeoxynucleotides on c-Jun and Jun-B protein expression. A: Western blots of NIH 3T3 cell lysate probed with an anti-c-jun antibody. B:SK-BR3 cell lysates, probed with an anti-jun-B antibody.

Incubation times with oligodeoxynucleotide were: Lanes 1-3: 6 h; Lanes 4-6: 24 h. Lanes 1 and 4: randomized control S-ODN; Lanes 2 and 5: anti-jun-B S-ODN-62; Lane 3 and 6: anti-c-jun S-ODN-13. 10 μg of total protein were used per lane.

FIG. 5

Effects of different phosphorothioate oligodeoxynucleotides on c-Jun, Jun-B and c-Fos protein expression.

A: Enzyme-linked immunosorbent assay of rat PC-12 cell lysates incubated with c-jun (rat specific) antisense oligodeoxynucleotides 174, 175, 176, 177.

B: Enzyme-linked immunosorbent assay of human SK-Br-3 cell lysates incubated with c-jun (human-specific) antisense oligodeoxynucleotides 1, 7, 13, 17, 20, 23, 26, 31, 31, 39, 45, 51 or 54.

C: Enzyme-linked immunosorbent assay of rat PC-12 cell lysates incubated with jun-B (rat-specific) antisense oligo-deoxynucleotides 178 or 179.

D: Enzyme-linked immunosorbent assay of human SK-Br-3 cell lysates incubated with jun-B (human-specific) antisense oligodeoxynucleotides 57, 62, 64, 69, 80 85, 89, 92, 95 or 97.

E: Enzyme-linked immunosorbent assay of rat PC-12 cell lysates incubated with c-fos (rat-specific) antisense oligodeoxynucleotides 180, 181, 182, 183, 184 or 185.

F: Enzyme-linked immunosorbent assay of human SK-Br-3 cell lysates incubated with c-fos (human-specific) antisense oligonucleotides 98, 99, 102, 103, 108, 116, 121, 130, 139, 144, 152, 158, 165, 170 or 173.

Phosphorothioate-oligodeoxynucleotides were used at 2 μM concentration. Control cells were left untreated (white bars) or treated with 2 μM of randomized control phosphorothioate oligonucleotides (grey bars).

FIG. 6

Survival of rat cerebellar neurons following hypoxia. Phosphorothioate oligonucleotides were used at 1 μM concentration. Control cells were not subjected to hypoxia (white bar). Hypoxia control cells were either not treated with oligonucleotide (black bar, C) or treated with the same concentration of randomized control phosphorothioate oligo-deoxynucleotide (grey bar). Error bars correspond to 1 SD.

FIG. 7

Enhanced proliferation arrest after suppression of c-Jun protein synthesis and lack of proliferation arrest in NGF treated PC-12 cells after suppression of Jun-B protein synthesis. PC-12 cell number after 8 days of NGF treatment. Bars represent the mean of 4 values. Grey bars: 2 μM randomized control S-ODN; White bars: 2 μM anti-c-jun S-ODN-174; Black bars: 2 μM anti-jun-B S-ODN-179. Error bars correspond to 1 SD.

FIG. 8

Morphological differentiation of NGF treated PC-12 cells after inhibition of c-jun or jun-B protein synthesis.

A: Control cells not treated with phosphorothioate oligo-deoxynucleotides.

B: Cells incubated with 2 μM anti-jun-B S-ODN-179.

C: Cells incubated with 2 μM anti-c-jun S-ODN-174.

The invention is further explained by he following non-limiting examples.

EXAMPLE 1

Cell Lines and Proliferation Assays

NIH 3T3 mouse fibroblasts and SK-Br-3 human mammary carcinoma cells were grown in RPMI medium (Gibco) supplemented with 100 U/ml penicillin, 100 μg/ml streptomycin, 5% FCS. PC-12 rat phaeochromocytoma cells were grown in Dulbecco's modified Eagle's medium (DMEM medium Seromed), supplemented with 100 U/ml penicillin, 100 μg/ml streptomycin, 5% FCS.

EXAMPLE 2

Western Blot

Cells were kept under low serum conditions in RPMI/2% FCS for 3 days, trypsinized and preincubated in RPMI/5% FCS/2 µM S-ODN for 5 min. 3×10$^6$ cells were plated into 260 ml culture flasks and grown for the times indicated in RPMI/5% FCS/2 µM S-ODN, trypsinized, spun down and lysed by freezing. SDS-polyacrylamide gel electrophoresis, blotting and chemiluminescence detection were performed according to standard techniques. Blots were probed with a rabbit anti mouse-c-jun antibody (Oncogene Science) or with a rabbit anti human-jun-B antibody (Oncogene Science) or with a rabbit anti-c-fos antibody (Oncogene Science), using goat anti-rabbit IgG-alkaline-phosphatase conjugate (Boehringer Mannheim) as second antibody and CSPD (Tropix) for chemiluminescent detection.

EXAMPLE 3

Enzyme-Linked Immunosorbent Assay (ELISA)

Cell lysates were diluted in 50 mM carbonate buffer at pH 9.0 and immobilized on immunon II plates (Dynatech Laboratories, Inc.) overnight. Antigen solution was removed and 200 µl/well phosphate buffered saline (PBS)/1% BSA/0.02% azide were added to block non-specific protein binding. Following incubation at room temperature for 2 h solution was removed. After washing with PBS plates were air dried for 3 h. Specific antibodies for c-jun, jun-B or c-fos (Oncogene, Santa Cruz, Biotechnology Inc.) were added at 50 µl/well, diluted in blocking buffer. Following 1 h incubation at room temperature samples were removed and subsequently wells were washed four times with PBS/0.05% Tween 20. Then 50 µl of secondary antibody-phosphatase conjugate were added and removed after 1 h. Wells were washed with diethanolamine buffer (10 mM diethanolamine, 0.5 mM MgCl$_2$, pH 9.5). 1 tablet of Sigma 104 phosphatase substrate was dissolved in 5 ml diethanolamine buffer. 50 µl of the substrate solution were added per well. The reaction was stopped with 50 µl 0.1 M EDTA (pH 7.5) and plates were read on a microtitration plate reader.

EXAMPLE 4

Neuronal Survival

Cerebella were removed from the brains of 8 day old rats under sterile conditions and were transferred into 0.1% trypsin, 0.1% DNase in phosphate buffered saline/glucose solution for 15 min at 20° C., followed by 1.5% soybean trypsin inhibitor (Sigma) for 5 min. Cells were dissociated in a mixture of Dulbecco's modified Eagle's medium and Ham's F-12 medium (50%/50%, v/v; DMEM F-12, Gibco) supplemented with KCl 25 mM, penicillin (5 U/ml), gentamycin (5 µg/ml) and 30 mM glucose. Cells were centrifuged at 300 x g for 3 min, and resuspended in the same medium, supplemented with 10% fetal calf serum (Gibco). Cells were plated in 3 cm dishes (0.5 ml per well) coated with poly-L-lysine (10 µg/ml, Sigma) to a density of 1×10$^5$ cells/well and transferred to an incubator with humidified atmosphere with 95% O$_2$/5% CO$_2$. Cytosine arabinoside (40 µM) was added after 24 h to inhibit glial cell proliferation. On day 16 after seeding, cells were exposed to anoxia for 16 h by placing them in a hermetic chamber containing a humidified atmosphere with 95% N$_2$/5% CO$_2$. The chamber was transferred into an incubator at 37° C. Phosphorothioate oligodeoxynucleotides were added at 1 µM concentration 8 h before the onset of anoxia. Neuronal cell injury was determined 26 h later by staining with trypan blue dye exclusion (incubation with 0.4% trypan blue for 5 min).

EXAMPLE 5

Proliferation of PC-12 Cells After Treatment with NGF and Different Phosphorothioate Oligodeoxynucleotides.

PC-12 cells were plated at a density of 2,500 cells/well in DMEM (Seromed) supplemented with 100 U/ml penicillin, 100 µg/ml streptomycin, 5% FCS/2 µM S-ODN. 2 µM S-ODNs were added 6 h after plating. 24 h after plating, cells were incubated with 10 ng/ml of the 2.5 S subfraction of nerve growth factor (NGF) (Boehringer Mannheim) for 8 days. Cell number was determined by using trypan blue dye exclusion (incubation with 0.4% trypan blue for 5 min) and counting of cells in a Neubauer counting chamber.

EXAMPLE 6

PC-12 Tumor Cell Differentiation

PC-12 cells were plated at a density of 2,500 cells/well (Seromed) into 96 well microtitration plates coated with poly-L-lysine (10 µg/ml, Sigma) in 100 µl of DMEM supplemented with 100 U/ml penicillin, 100 µg/ml streptomycin, 5% FCS, S-ODNs were added at 2 µM concentration 2 h after plating. 6 h after plating, cells were incubated with 40 ng/ml of the 2.5 S subfraction of nerve growth factor (NGF) (Boehringer Mannheim) for 11 days.

---

The invention claimed is:

1. An antisense oligonucleotide, wherein the antisense oligonucleotide is SEQ ID NO: 2, the antisense oligonucleotide being, optionally, substituent-modified, or phosphorothioated, or substituent-modified and phosphorothioated.

2. A composition for human administration comprising the antisense oligonucleotide of claim 1 together with a physiologically acceptable carrier.

* * * * *

SEQUENCE LISTING (1) GENERAL INFORMATION:

(iii) NUMBER OF SEQUENCES: 185

(2) INFORMATION FOR SEQ ID NO: 1:

(i) SEQUENCE CHARACTERISTICS:
      (A) LENGTH: 14 base pairs
      (B) TYPE: nucleic acid
      (C) STRANDEDNESS: unknown -continued (D) TOPOLOGY: unknown (ii) MOLECULE TYPE: DNA (genomic)

(iii) ANTI-SENSE: YES (xi) SEQUENCE DESCRIPTION: SEQ ID NO: 1:

TCGGACTATA CTGC                                              14

(2) INFORMATION FOR SEQ ID NO: 2:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 2:

CAGTTCGGAC TATACT                                            16

(2) INFORMATION FOR SEQ ID NO: 3:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 3:

AAGCCTAAGA CGCA                                              14

(2) INFORMATION FOR SEQ ID NO: 4:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 4:

GCCCAAGTTC AACA                                              14

(2) INFORMATION FOR SEQ ID NO: 5:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 5:

TGAAAAGTCG CGGT                                              14

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 6:

GGTTAATTAA GATGCCTC                      18

(2) INFORMATION FOR SEQ ID NO: 7:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 7:

TCTCTAAGAG CGCA                          14

(2) INFORMATION FOR SEQ ID NO: 8:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 8:

ACGTGAGGTT AGTTTG                        16

(2) INFORMATION FOR SEQ ID NO: 9:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 9:

CACGTGAGGT TAGT                          14

(2) INFORMATION FOR SEQ ID NO: 10:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 10:

CATAGAACAG TCCG                                                              14

(2) INFORMATION FOR SEQ ID NO: 11:

(i) SEQUENCE CHARACTERISTICS:
          (A) LENGTH: 16 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 11:

CAGTCATAGA ACAGTC                                                            16

(2) INFORMATION FOR SEQ ID NO: 12:

(i) SEQUENCE CHARACTERISTICS:
          (A) LENGTH: 18 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 12:

CTTTGCAGTC ATAGAACA                                                          18

(2) INFORMATION FOR SEQ ID NO: 13:

(i) SEQUENCE CHARACTERISTICS:
          (A) LENGTH: 14 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 13:

TGCAGTCATA GAAC                                                              14

(2) INFORMATION FOR SEQ ID NO: 14:

(i) SEQUENCE CHARACTERISTICS:
          (A) LENGTH: 14 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 14:

GGTCGTTTCC ATCT                                                              14

(2) INFORMATION FOR SEQ ID NO: 15:

(i) SEQUENCE CHARACTERISTICS:
          (A) LENGTH: 16 base pairs
          (B) TYPE: nucleic acid

```
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 15:

CATAGAAGGT CGTTTC                                                      16

(2) INFORMATION FOR SEQ ID NO: 16:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 16:

CGTCATAGAA GGTC                                                        14

(2) INFORMATION FOR SEQ ID NO: 17:

(i) SEQUENCE CHARACTERISTICS:
        (A) LENGTH: 15 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 17:

CATCGTCATA GAAGG                                                       15

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 18:

GGACGGGAGG AACGAGGCGT TGAG                                             24

(2) INFORMATION FOR SEQ ID NO: 19:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 19:

TAGCCATAAG GTCC                                                        14
```

(2) INFORMATION FOR SEQ ID NO: 20:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 20:

GGTTACTGTA GCCA                                                              14

(2) INFORMATION FOR SEQ ID NO: 21:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 21:

GGTTACTGTA GCCA                                                              14

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 22:

CAGGGTCATG CTCTGTTTCA GGATCTTGGG                                              30

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 23:

AGTTCTTGGC GCGGAGGT                                                          18

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 24:

AGGTGAGGAG GTCCGAGT                                                      18

(2) INFORMATION FOR SEQ ID NO: 25:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 25:

TGGACTGGAT TATCAG                                                        16

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 26:

GTGGTGGTGA TGTGCCCG                                                      18

(2) INFORMATION FOR SEQ ID NO: 27:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 27:

TGTCACGTTC TTGG                                                          14

(2) INFORMATION FOR SEQ ID NO: 28:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 28:

CTCATCTGTC ACGT                                                          14

(2) INFORMATION FOR SEQ ID NO: 29:

(i) SEQUENCE CHARACTERISTICS:
        (A) LENGTH: 18 base pairs

```
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 29:

CGAAGCCCTC GGCGAACC                                                    18

(2) INFORMATION FOR SEQ ID NO: 30:

(i) SEQUENCE CHARACTERISTICS:
            (A) LENGTH: 24 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 30:

GCGTGTTCTG GCTGTGCAGT TCGG                                             24

(2) INFORMATION FOR SEQ ID NO: 31:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 31:

CTGCCCCGTT GACC                                                        14

(2) INFORMATION FOR SEQ ID NO: 32:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 32:

AGGTTTGCGT AGAC                                                        14

(2) INFORMATION FOR SEQ ID NO: 33:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 33:

GGTTGAAGTT GCTG                                                        14
```

(2) INFORMATION FOR SEQ ID NO: 34:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 34:

CTGGGTTGAA GTTG     14

(2) INFORMATION FOR SEQ ID NO: 35:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 35:

TGCTGGGGTT GCGCGGGAAA GGCC     24

(2) INFORMATION FOR SEQ ID NO: 36:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 36:

TGCTGCACGG GCATCTGCTG     20

(2) INFORMATION FOR SEQ ID NO: 37:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 37:

GGCACTGTCT GAGGCTCCTC CTTCAGG     27

(2) INFORMATION FOR SEQ ID NO: 38:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 38:

ACTCCATGTC GATG                                                                      14

(2) INFORMATION FOR SEQ ID NO: 39:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 39:

CTCTCCGCCT TGATCC                                                                    16

(2) INFORMATION FOR SEQ ID NO: 40:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 40:

GTTCCTCATG CGCTTC                                                                    16

(2) INFORMATION FOR SEQ ID NO: 41:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 41:

CTGAGCTTTC AAGG                                                                      14

(2) INFORMATION FOR SEQ ID NO: 42:

(i) SEQUENCE CHARACTERISTICS:
            (A) LENGTH: 26 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 42:

GCGATTCTCT CCAGCTTCCT TTTTCG                                                         26

(2) INFORMATION FOR SEQ ID NO: 43:

(i) SEQUENCE CHARACTERISTICS:

```
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 43:

CTGAGCTTTC AAGGTTTTCA CTTTTTCCTC                                          30

(2) INFORMATION FOR SEQ ID NO: 44:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 44:

TCCCTGAGCA TGTT                                                           14

(2) INFORMATION FOR SEQ ID NO: 45:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 45:

TCTGTTTAAG CTGTGC                                                         16

(2) INFORMATION FOR SEQ ID NO: 46:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 46:

CTTTCTGTTT AAGCTGTG                                                       18

(2) INFORMATION FOR SEQ ID NO: 47:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 47:
```

```
GGTTCATGAC TTTCTG                                                              16

(2) INFORMATION FOR SEQ ID NO: 48:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 48:

CGTGGTTCAT GACT                                                                14

(2) INFORMATION FOR SEQ ID NO: 49:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 49:

ACTGTTAACG TGGTTC                                                              16

(2) INFORMATION FOR SEQ ID NO: 50:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 50:

CCACTGTTAA CGTG                                                                14

(2) INFORMATION FOR SEQ ID NO: 51:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 51:

CCCACTGTTA ACGT                                                                14

(2) INFORMATION FOR SEQ ID NO: 52:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown
```

(ii) MOLECULE TYPE: DNA (genomic)

(iii) ANTI-SENSE: YES (xi) SEQUENCE DESCRIPTION: SEQ ID NO: 52:

AGCATGAGTT GGCA                                                              14

(2) INFORMATION FOR SEQ ID NO: 53:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 53:

GCGTTAGCAT GAGT                                                              14

(2) INFORMATION FOR SEQ ID NO: 54:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 54:

GTTTGCAACT GCTG                                                              14

(2) INFORMATION FOR SEQ ID NO: 55:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 55:

CAAAATGTTT GCAACTGC                                                          18

(2) INFORMATION FOR SEQ ID NO: 56:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 56:

TCCATTTTAG TGCACATC                                                          18

(2) INFORMATION FOR SEQ ID NO: 57:

```
    (i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 57:

CTGTTCCATT TTAGTGCA                                                         18

(2) INFORMATION FOR SEQ ID NO: 58:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 58:

GTGTATGAGT CGTC                                                             14

(2) INFORMATION FOR SEQ ID NO: 59:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 59:

CTGTGTATGA GTCG                                                             14

(2) INFORMATION FOR SEQ ID NO: 60:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 60:

CGTAGCTGTG TATG                                                             14

(2) INFORMATION FOR SEQ ID NO: 61:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 61:
```

TCGTGTAGAG AGAG                                                      14

(2) INFORMATION FOR SEQ ID NO: 62:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 62:

AGTTTGTAGT CGTGTAGA                                                  18

(2) INFORMATION FOR SEQ ID NO: 63:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 63:

GTTTGTAGTC GTGTAG                                                    16

(2) INFORMATION FOR SEQ ID NO: 64:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 64:

AGTTTGTAGT CGTG                                                      14

(2) INFORMATION FOR SEQ ID NO: 65:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 65:

GGAGTTTGTA GTCG                                                      14

(2) INFORMATION FOR SEQ ID NO: 66:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 66:

TCAGGAGTTT GTAGTC                                                            16

(2) INFORMATION FOR SEQ ID NO: 67:

(i) SEQUENCE CHARACTERISTICS:
　　　　(A) LENGTH: 18 base pairs
　　　　(B) TYPE: nucleic acid
　　　　(C) STRANDEDNESS: unknown
　　　　(D) TOPOLOGY: unknown (ii) MOLECULE TYPE: DNA (genomic)

(iii) ANTI-SENSE: YES (xi) SEQUENCE DESCRIPTION: SEQ ID NO: 67:

GTTTCAGGAG TTTGTAGT                                                          18

(2) INFORMATION FOR SEQ ID NO: 68:

(i) SEQUENCE CHARACTERISTICS:
　　　　(A) LENGTH: 14 base pairs
　　　　(B) TYPE: nucleic acid
　　　　(C) STRANDEDNESS: unknown
　　　　(D) TOPOLOGY: unknown (ii) MOLECULE TYPE: DNA (genomic)

(iii) ANTI-SENSE: YES (xi) SEQUENCE DESCRIPTION: SEQ ID NO: 68:

TCGGTTTCAG GAGT                                                              14

(2) INFORMATION FOR SEQ ID NO: 69:

(i) SEQUENCE CHARACTERISTICS:
　　　　(A) LENGTH: 14 base pairs
　　　　(B) TYPE: nucleic acid
　　　　(C) STRANDEDNESS: unknown
　　　　(D) TOPOLOGY: unknown (ii) MOLECULE TYPE: DNA (genomic)

(iii) ANTI-SENSE: YES (xi) SEQUENCE DESCRIPTION: SEQ ID NO: 69:

TTGAGACTCC GGTA                                                              14

(2) INFORMATION FOR SEQ ID NO: 70:

(i) SEQUENCE CHARACTERISTICS:
　　　　(A) LENGTH: 16 base pairs
　　　　(B) TYPE: nucleic acid
　　　　(C) STRANDEDNESS: unknown
　　　　(D) TOPOLOGY: unknown (ii) MOLECULE TYPE: DNA (genomic)

(iii) ANTI-SENSE: YES (xi) SEQUENCE DESCRIPTION: SEQ ID NO: 70:

ACCAGAAAAG TAGCTG                                                            16

(2) INFORMATION FOR SEQ ID NO: 71:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 71:

CCTGACCAGA AAAG                                                         14

(2) INFORMATION FOR SEQ ID NO: 72:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 72:

ATTCAGGCGT TCCA                                                         14

(2) INFORMATION FOR SEQ ID NO: 73:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 73:

CTGTTGGGGA CAAT                                                         14

(2) INFORMATION FOR SEQ ID NO: 74:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 74:

GGTAAAAGTA CTGTCC                                                       16

(2) INFORMATION FOR SEQ ID NO: 75:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES

```
       (xi) SEQUENCE DESCRIPTION: SEQ ID NO: 75:

GGGTAAAAGT ACTGTC                                                          16

(2) INFORMATION FOR SEQ ID NO: 76:

(i) SEQUENCE CHARACTERISTICS:
           (A) LENGTH: 18 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 76:

GCACCTCCAC CGCTGCCA                                                        18

(2) INFORMATION FOR SEQ ID NO: 77:

(i) SEQUENCE CHARACTERISTICS:
           (A) LENGTH: 18 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 77:

CTCCTGCTCC TCGGTGAC                                                        18

(2) INFORMATION FOR SEQ ID NO: 78:

(i) SEQUENCE CHARACTERISTICS:
           (A) LENGTH: 14 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 78:

GCTTTGACAA AGCC                                                            14

(2) INFORMATION FOR SEQ ID NO: 79:

(i) SEQUENCE CHARACTERISTICS:
           (A) LENGTH: 14 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 79:

CTTGTGCAGA TCGT                                                            14

(2) INFORMATION FOR SEQ ID NO: 80:

(i) SEQUENCE CHARACTERISTICS:
           (A) LENGTH: 16 base pairs
           (B) TYPE: nucleic acid
           (C) STRANDEDNESS: unknown
```

(D) TOPOLOGY: unknown (ii) MOLECULE TYPE: DNA (genomic)

(iii) ANTI-SENSE: YES (xi) SEQUENCE DESCRIPTION: SEQ ID NO: 80:

TCATCTTGTG CAGATC                                                         16

(2) INFORMATION FOR SEQ ID NO: 81:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 81:

GTTCATCTTG TGCAGA                                                         16

(2) INFORMATION FOR SEQ ID NO: 82:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 82:

CGTGGTTCAT CTTG                                                           14

(2) INFORMATION FOR SEQ ID NO: 83:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 83:

TCACGTGGTT CATC                                                           14

(2) INFORMATION FOR SEQ ID NO: 84:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 84:

GCCCAGGGAC ACGTTGGG                                                       18

(2) INFORMATION FOR SEQ ID NO: 85:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 85:

GGTTGGTGTA AACG                                        14

(2) INFORMATION FOR SEQ ID NO: 86:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 86:

TACGAGCTCC CGGTCCCGAC                                20

(2) INFORMATION FOR SEQ ID NO: 87:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 87:

TAGCTGATGG TGGT                                        14

(2) INFORMATION FOR SEQ ID NO: 88:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 88:

CAGCTGCGCC GGGTGGCCAC CGGCGAAGGG                    30

(2) INFORMATION FOR SEQ ID NO: 89:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 89:

TCCTTGAAGG TGGA                                                             14

(2) INFORMATION FOR SEQ ID NO: 90:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 90:

TCTTCCATGT TGATGG                                                           16

(2) INFORMATION FOR SEQ ID NO: 91:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 91:

CTTTGATGCG CTCT                                                             14

(2) INFORMATION FOR SEQ ID NO: 92:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 92:

CTCCACTTTG ATGC                                                             14

(2) INFORMATION FOR SEQ ID NO: 93:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 93:

GCTCCAGCTT CCGCTTCCGG CACTTGGTGG                                             30

(2) INFORMATION FOR SEQ ID NO: 94:

(i) SEQUENCE CHARACTERISTICS:
        (A) LENGTH: 30 base pairs
        (B) TYPE: nucleic acid

```
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 94:

GGCCTTGAGC GTCTTCACCT TGTCCTCCAG                                      30

(2) INFORMATION FOR SEQ ID NO: 95:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 95:

TGACCTTCTG TTTGAG                                                     16

(2) INFORMATION FOR SEQ ID NO: 96:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 96:

CATGACCTTC TGTTTG                                                     16

(2) INFORMATION FOR SEQ ID NO: 97:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 97:

GTCATGACCT TCTG                                                       14

(2) INFORMATION FOR SEQ ID NO: 98:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 98:

CGAGAACATC ATCG                                                       14
```

(2) INFORMATION FOR SEQ ID NO: 99:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 99:

GTAGTCTGCG TTGA                                                              14

(2) INFORMATION FOR SEQ ID NO: 100:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 100:

GCTGCAGCGG GAGGATGACG                                                        20

(2) INFORMATION FOR SEQ ID NO: 101:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 101:

AGTAAGAGAG GCTATC                                                            16

(2) INFORMATION FOR SEQ ID NO: 102:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 102:

GTAGTAAGAG AGGC                                                              14

(2) INFORMATION FOR SEQ ID NO: 103:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 103:

GGTAGTAAGA GAGG                                                        14

(2) INFORMATION FOR SEQ ID NO: 104:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 104:

GTGAGTGGTA GTAAGA                                                      16

(2) INFORMATION FOR SEQ ID NO: 105:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 105:

GTCCGTGCAG AAGTCCTG                                                    18

(2) INFORMATION FOR SEQ ID NO: 106:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 106:

GAATGAAGTT GGCACT                                                      16

(2) INFORMATION FOR SEQ ID NO: 107:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 107:

GGAATGAAGT TGGC                                                        14

(2) INFORMATION FOR SEQ ID NO: 108:

(i) SEQUENCE CHARACTERISTICS:
        (A) LENGTH: 14 base pairs

-continued

```
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 108:

GGGAATGAAG TTGG                                                      14

(2) INFORMATION FOR SEQ ID NO: 109:

(i) SEQUENCE CHARACTERISTICS:
            (A) LENGTH: 30 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 109:

GCTGCACCAG CCACTGCAGG TCCGGACTGG                                      30

(2) INFORMATION FOR SEQ ID NO: 110:

(i) SEQUENCE CHARACTERISTICS:
            (A) LENGTH: 30 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 110:

CTGGTCTGCG ATGGGGCCAC AGAGGAGACG                                      30

(2) INFORMATION FOR SEQ ID NO: 111:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 111:

TCATGGTCTT CACAAC                                                    16

(2) INFORMATION FOR SEQ ID NO: 112:

(i) SEQUENCE CHARACTERISTICS:
            (A) LENGTH: 30 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 112:

CAATGCTCTG CGCTCGGCCT CCTGTCATGG                                      30
```

(2) INFORMATION FOR SEQ ID NO: 113:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 113:

CTAGAGTTCC TCAC                                              14

(2) INFORMATION FOR SEQ ID NO: 114:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 114:

GAGTACGCTA GAGT                                              14

(2) INFORMATION FOR SEQ ID NO: 115:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 115:

GAAGAGTACG CTAG                                              14

(2) INFORMATION FOR SEQ ID NO: 116:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 116:

CTGCTTCCCA CCCAGCCCCC ACATTCCC                               28

(2) INFORMATION FOR SEQ ID NO: 117:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 117:

TTCATCCTCT GTACTGGGCT                                                    20

(2) INFORMATION FOR SEQ ID NO: 118:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 118:

GTTACGGATG TGCA                                                          14

(2) INFORMATION FOR SEQ ID NO: 119:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 119:

CAGTTACGGA TGTG                                                          14

(2) INFORMATION FOR SEQ ID NO: 120:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 120:

CCAGTTACGG ATGT                                                          14

(2) INFORMATION FOR SEQ ID NO: 121:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 121:

AGAGTCTGAG TTGG                                                          14

(2) INFORMATION FOR SEQ ID NO: 122:

(i) SEQUENCE CHARACTERISTICS:

(A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 122:

GTGAGACTCA GAGT                                                              14

(2) INFORMATION FOR SEQ ID NO: 123:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 123:

TCTTAGGGTG AGAC                                                              14

(2) INFORMATION FOR SEQ ID NO: 124:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 124:

GAGAGTACTT CTTAGG                                                            16

(2) INFORMATION FOR SEQ ID NO: 125:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 125:

GGAAGAAACT ATGAGAGT                                                          18

(2) INFORMATION FOR SEQ ID NO: 126:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 126:

CTTAGGGAAG AAACTATG                                                       18

(2) INFORMATION FOR SEQ ID NO: 127:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 127:

CGGTAAGAAA CTTAGG                                                         16

(2) INFORMATION FOR SEQ ID NO: 128:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 128:

AGCATGCGGT AAGA                                                           14

(2) INFORMATION FOR SEQ ID NO: 129:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 129:

GTCTGAAAGC ATGC                                                           14

(2) INFORMATION FOR SEQ ID NO: 130:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 130:

AGAACAAAGA AGAGCC                                                         16

(2) INFORMATION FOR SEQ ID NO: 131:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown -continued (ii) MOLECULE TYPE: DNA (genomic)

(iii) ANTI-SENSE: YES (xi) SEQUENCE DESCRIPTION: SEQ ID NO: 131:

CAAGAGAACA AGAAGAG                                                     18

(2) INFORMATION FOR SEQ ID NO: 132:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 132:

CAGCAAGAGA ACAAAG                                                      16

(2) INFORMATION FOR SEQ ID NO: 133:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 133:

TCCTCAGCAA GAGA                                                        14

(2) INFORMATION FOR SEQ ID NO: 134:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 134:

AGGTGTGACT TGCA                                                        14

(2) INFORMATION FOR SEQ ID NO: 135:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 135:

GAATAGGTGT GACTTG                                                 16

(2) INFORMATION FOR SEQ ID NO: 136:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 136:

CAGAATAGGT GTGACT                                                          16

(2) INFORMATION FOR SEQ ID NO: 137:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 137:

GCAGAATAGG TGTG                                                            14

(2) INFORMATION FOR SEQ ID NO: 138:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 138:

CAGTTGCAGA ATAGGT                                                          16

(2) INFORMATION FOR SEQ ID NO: 139:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 139:

GAAACCATTT CTGACC                                                          16

(2) INFORMATION FOR SEQ ID NO: 140:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 140:

TGTGAAACCA TTTCTGAC					18

(2) INFORMATION FOR SEQ ID NO: 141:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 141:

CACTGTGAAA CCATTTCT					18

(2) INFORMATION FOR SEQ ID NO: 142:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 142:

CCACTGTGAA ACCA						14

(2) INFORMATION FOR SEQ ID NO: 143:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 143:

AGAACTGGCT CCTGCAGCTT CCCTGCTTCC			30

(2) INFORMATION FOR SEQ ID NO: 144:

(i) SEQUENCE CHARACTERISTICS:
        (A) LENGTH: 15 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 144:

CACCTCCATT CACCC					15

(2) INFORMATION FOR SEQ ID NO: 145:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown -continued (ii) MOLECULE TYPE: DNA (genomic)

(iii) ANTI-SENSE: YES (xi) SEQUENCE DESCRIPTION: SEQ ID NO: 145:

CAGTAAAAGT GTCTGC                                      16

(2) INFORMATION FOR SEQ ID NO: 146:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 146:

CGACATTCAG TAAAAGTG                                    18

(2) INFORMATION FOR SEQ ID NO: 147:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 147:

GACCGACATT CAGT                                        14

(2) INFORMATION FOR SEQ ID NO: 148:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 148:

CTTCTGGAGA TAACTAGA                                    18

(2) INFORMATION FOR SEQ ID NO: 149:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 149:

CATCTTATTC CTTTCCCT                                    18

(2) INFORMATION FOR SEQ ID NO: 150:

(i) SEQUENCE CHARACTERISTICS:
    (A) LENGTH: 16 base pairs
    (B) TYPE: nucleic acid
    (C) STRANDEDNESS: unknown
    (D) TOPOLOGY: unknown (ii) MOLECULE TYPE: DNA (genomic)

(iii) ANTI-SENSE: YES (xi) SEQUENCE DESCRIPTION: SEQ ID NO: 150:

CAGCCATCTT ATTCCT                                                          16

(2) INFORMATION FOR SEQ ID NO: 151:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 151:

TGCAGCCATC TTATTC                                                          16

(2) INFORMATION FOR SEQ ID NO: 152:

(i) SEQUENCE CHARACTERISTICS:
        (A) LENGTH: 15 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 152:

GAGTGTATCA GTCAG                                                           15

(2) INFORMATION FOR SEQ ID NO: 153:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 153:

GGAGTGTATC AGTC                                                            14

(2) INFORMATION FOR SEQ ID NO: 154:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 154:

CTTGGAGTGT ATCAGT                                                                16

(2) INFORMATION FOR SEQ ID NO: 155:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 155:

ACAGAGTACC TACC                                                                  14

(2) INFORMATION FOR SEQ ID NO: 156:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 156:

CCAACTTTCC CTTAAG                                                                16

(2) INFORMATION FOR SEQ ID NO: 157:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 157:

CCTTATGCTC AATCTC                                                                16

(2) INFORMATION FOR SEQ ID NO: 158:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 158:

GTCTTACTCA AGGG                                                                  14

(2) INFORMATION FOR SEQ ID NO: 159:

(i) SEQUENCE CHARACTERISTICS:
            (A) LENGTH: 16 base pairs
            (B) TYPE: nucleic acid
            (C) STRANDEDNESS: unknown (D) TOPOLOGY: unknown (ii) MOLECULE TYPE: DNA (genomic)

(iii) ANTI-SENSE: YES (xi) SEQUENCE DESCRIPTION: SEQ ID NO: 159:

ACAGTCTTAC TCAAGG                                                       16

(2) INFORMATION FOR SEQ ID NO: 160:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 160:

CATAAGACAC AGTCTTAC                                                     18

(2) INFORMATION FOR SEQ ID NO: 161:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 161:

GAAAGCATAA GACACAGT                                                     18

(2) INFORMATION FOR SEQ ID NO: 162:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 162:

GGAAAGCATA AGACAC                                                       16

(2) INFORMATION FOR SEQ ID NO: 163:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 163:

AGGGATAAAG GAAAGC                                                       16

(2) INFORMATION FOR SEQ ID NO: 164:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 164:

CCTGTATACA GAGG                                                            14

(2) INFORMATION FOR SEQ ID NO: 165:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 165:

TGTCTCCTGT ATACAG                                                          16

(2) INFORMATION FOR SEQ ID NO: 166:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 166:

CATCTTCTAG TTGGTC                                                          16

(2) INFORMATION FOR SEQ ID NO: 167:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 167:

CTCATCTTCT AGTTGG                                                          16

(2) INFORMATION FOR SEQ ID NO: 168:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 168:

CTTCTCATCT TCTAGTTG                                    18

(2) INFORMATION FOR SEQ ID NO: 169:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 169:

CAAAGCAGAC TTCTCA                                      16

(2) INFORMATION FOR SEQ ID NO: 170:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 170:

CTGCAAAGCA GACT                                        14

(2) INFORMATION FOR SEQ ID NO: 171:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 171:

CTAGTTTTTC CTTCTCCT                                    18

(2) INFORMATION FOR SEQ ID NO: 172:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 172:

TCTAGTTTTT CCTTCTCC                                    18

(2) INFORMATION FOR SEQ ID NO: 173:

(i) SEQUENCE CHARACTERISTICS:
        (A) LENGTH: 16 base pairs
        (B) TYPE: nucleic acid

```
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 173:

CAGGATGAAC TCTAGT                                                  16

(2) INFORMATION FOR SEQ ID NO: 174:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 174:

TCGTAGAAGG TCGT                                                    14

(2) INFORMATION FOR SEQ ID NO: 175:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 175:

AGGGTTACTG TAGC                                                    14

(2) INFORMATION FOR SEQ ID NO: 176:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 176:

GTAGTGGTGA TGTG                                                    14

(2) INFORMATION FOR SEQ ID NO: 177:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 177:

CGTCGTAGAA GGTC                                                    14
```

```
(2) INFORMATION FOR SEQ ID NO: 178:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 178:

TTTCGTGCAC ATCC                                                    14

(2) INFORMATION FOR SEQ ID NO: 179:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 179:

AGTTTGTAGT CGTGAAGA                                                18

(2) INFORMATION FOR SEQ ID NO: 180:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 180:

CGAGAACATC ATGG                                                    14

(2) INFORMATION FOR SEQ ID NO: 181:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 181:

GTAGTAGGAA AGGC                                                    14

(2) INFORMATION FOR SEQ ID NO: 182:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)
```

-continued (iii) ANTI-SENSE: YES (xi) SEQUENCE DESCRIPTION: SEQ ID NO: 182:

GGTAGTAGGA AAGG                                                            14

(2) INFORMATION FOR SEQ ID NO: 183:

(i) SEQUENCE CHARACTERISTICS:
       (A) LENGTH: 14 base pairs
       (B) TYPE: nucleic acid
       (C) STRANDEDNESS: unknown
       (D) TOPOLOGY: unknown (ii) MOLECULE TYPE: DNA (genomic)

(iii) ANTI-SENSE: YES (xi) SEQUENCE DESCRIPTION: SEQ ID NO: 183:

GGAATGGTAG TAGG                                                            14

(2) INFORMATION FOR SEQ ID NO: 184:

(i) SEQUENCE CHARACTERISTICS:
       (A) LENGTH: 15 base pairs
       (B) TYPE: nucleic acid
       (C) STRANDEDNESS: unknown
       (D) TOPOLOGY: unknown (ii) MOLECULE TYPE: DNA (genomic)

(iii) ANTI-SENSE: YES (xi) SEQUENCE DESCRIPTION: SEQ ID NO: 184:

GGTCATTGAG AAGAG                                                           15

(2) INFORMATION FOR SEQ ID NO: 185:

(i) SEQUENCE CHARACTERISTICS:
       (A) LENGTH: 16 base pairs
       (B) TYPE: nucleic acid
       (C) STRANDEDNESS: unknown
       (D) TOPOLOGY: unknown (ii) MOLECULE TYPE: DNA (genomic)

(iii) ANTI-SENSE: YES (xi) SEQUENCE DESCRIPTION: SEQ ID NO: 185:

GCTAATGTTC TTGACC                                                          16